United States Patent
Negahdaripour et al.

(10) Patent No.: US 6,236,459 B1
(45) Date of Patent: *May 22, 2001

(54) THIN FILM MEASURING DEVICE AND METHOD

(75) Inventors: Shahriar Negahdaripour, Coral Gables; Ali Khamene, South Miami, both of FL (US)

(73) Assignee: University of Miami, Miami, FL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/186,428

(22) Filed: Nov. 5, 1998

(51) Int. Cl.[7] ................................................ G01B 9/02

(52) U.S. Cl. .................................... 356/357; 356/346

(58) Field of Search ............................. 356/346, 345, 356/357

(56) References Cited

U.S. PATENT DOCUMENTS

| | | |
|---|---|---|
| 4,221,486 | 9/1980 | Jaerisch et al. . |
| 4,672,196 | 6/1987 | Canino . |
| 4,676,647 | 6/1987 | Kikkawa et al. . |
| 5,091,647 | 2/1992 | Carduner et al. . |
| 5,121,337 | 6/1992 | Brown . |
| 5,328,787 | * 7/1994 | Clifford et al. . |
| 5,333,052 | 7/1994 | Finarov . |
| 5,486,701 | 1/1996 | Norton et al. . |
| 5,610,392 | 3/1997 | Nagayama et al. . |
| 5,905,574 | * 5/1999 | Vollbrecht et al. .................. 356/345 |

FOREIGN PATENT DOCUMENTS 0 660 076 A2   6/1995   (EP) .

OTHER PUBLICATIONS

Doane, "An Instrument for In Vivo Tear Film Interferometry", *Optometry and Vision Science*, vol. 66, No. 6, Jun. 1989, pp. 383–388.

Josephson, "Appearance of the Preocular Tear Film Lipid Layer", *American Journal of Optometry and Physiological Optics*, vol. 60, No. 11, Nov. 1983, pp. 883–887.

Vora et al, "Mathematical Methods for the Analysis of Color Scanning Filters", *Image Processing*, vol. 6, No. 2, IIPRE4, Feb. 1997, pp. 321–327.

Healey, "Color Discrimination By Computer",*Color*,©1992, Jones and Bartlett Publishers, Inc., pp. 129–133.

Yokoi et al, "Correlation of Tear Lipid Layer Interference Patterns with the Diagnosis and Severity of Dry Eye", *American Journal of Ophthalmology*, vol. 122, Dec. 1996, pp. 818–824.

Prydal et al, "Study of Human Precorneal Tear Film Thickness and Structure Using Laser Interferometry",*Investigative Ophthalmology & Visual Science*, vol. 33, No. 6, May 1992, pp. 2006–2011.

Ruben et al, Ed., *Contact Lens Practice*,©1994, pp. 173–175, 345–347, 349–352, 426–429, 463–466.

* cited by examiner

Primary Examiner—Frank G. Font
Assistant Examiner—Andrew H. Lee
(74) Attorney, Agent, or Firm—Pillsbury Madison & Sutro LLP (57) ABSTRACT

An interferometric thin film measuring device has a source of illumination light, a detector disposed in a return path of light reflected from a specimen of illumination light, a plurality of wavelength filters that filter light into image channels, a weight vector calculating device that receives detected signals, a look-up table storage unit that stores calibration weight vectors, a weight vector comparing unit that compares calibration weight vectors from the look-up table storage unit to subject weight vectors, and a data output/storage unit to output the measured thin film values.

34 Claims, 9 Drawing Sheets

THIN FILM MEASURING DEVICE AND METHOD

BACKGROUND OF THE INVENTION

1. Field of the Invention

The present invention pertains to a thin film measuring device and method, and more particularly to a thin film measuring device and method that provides real time and/or spatially extended thin film thickness measurements.

2. Description of the Related Art

There are a large number of conventional devices which use interference effects to measure physical properties of various materials or bodies. Fizeau fringes have long been known to provide information regarding the thickness of thin films which are at least partially transparent to the illumination radiation. Fizeau fringes are produced by the interference of electromagnetic waves that are reflected from a first incident surface with electromagnetic waves reflected from a second incident surface of the thin film. When the two waves are coherent, a series of bright and dark bands are produced, often referred to as a fringe pattern, which correspond to contours of constant optical thickness of the thin film. If the thin film is illuminated with coherent monochromatic light, a fringe pattern of light and dark bands are produced. On the other hand, if the thin film is illuminated with white light or light that has a plurality of spectral bands, then a pattern of colored bands are produced, provided that the light source is sufficiently coherent on the scale of the film thickness. In the case of color fringes, contours of constant color indicate regions of constant thin film thickness. Examples of color fringes in everyday experience are the color fringes produced by light reflected by soap bubbles or light reflected from a puddle of water with a thin film of oil floating on top.

There are a large variety of conventional devices available for producing and recording interference patterns from various thin films. However, one is then left with an image of a pattern that may extend over a region of the thin film and may be dynamic in that the pattern changes in time according to changes in the film thickness over time.

An example of such a spatially extended and dynamic thin film is that of the tear film of a subject's eye. The tear film is believed to be approximately a two-layer film covering the cornea of the eye. The outer layer of the tear film is a very thin oily layer known as the lipid layer. The stability of the pre-corneal tear film is thought to result from interactions between its three major components: mucus glycoprotein, aqueous phase, and superficial Meibomain oils. Clinicians can gather useful information from observations of different aspects of the tear film. Examination of the lipid layer can be helpful in establishing the prognosis of prospective contact lens patients, anticipating special contact-lens-related problems, and in the analysis of symptoms of non-contact lens wearing patients.

The thickness of the lipid layer is believed to be a very informative cue of its stability which is useful in uncovering disorders. Examples of conventional devices for measuring static and dynamic properties of tear films are provided in Josephson, J. E., "Appearance of the Preocular Tear Film Lipid Layer", American Journal of Optometry and Physiological Optics, vol. 60, no. 11, pages 883–887, 1993 and Hamano et al., "Bio-differential Interference Microscope Observation on Anterior Segment of the Eye", Journal of Japanese Contact Lens Society vol. 21, pages 229–246, 1979. Such prior art devices are specially adapted to forming interference fringes from the tear film of a subject's eye. However, such prior art devices merely record the interference fringes as a video image. This leaves one with the task of extracting the quantitative film thickness information from the video image, over an extended spatial region of the image at a given time, at a given point in the image over time, or both over an extended spatial region for a period of time to produce film thickness contours which may change over time.

Another problem encountered in measuring the lipid layer of a subject's eye, is that the lipid layer does not normally produce color fringe patterns even though it is illuminated with sufficiently coherent white light. However, color patterns are observed when the lipid layer is thickened during blinking. This indicates that the lipid layer is typically very thin relative to visible light. In this case, the fringes appear to vary in intensity, without varying in color. Consequently, a problem with extracting information from interference patterns of the lipid layer is that one cannot determine the thicknesses in the range of interest based purely on the color of the fringes. On the other hand, a monochromatic interference pattern does not provide the additional information obtainable with a white light, or multiband source for the thicker thin films.

SUMMARY OF THE INVENTION

Accordingly, it is an object of this invention to provide an interferometric thin film measuring device which provides quantitative thin film thickness determinations over a spatially extended region of a thin film.

It is another object of this invention to provide an interferometric thin film measuring device that provides real time thin film thicknesses of a thin film.

It is another object of this invention to provide an interferometric thin film measuring device that provides real time thin film thicknesses over a spatially extended region of a thin film for a plurality of different times.

It is another object of this invention to provide an interferometric thin film measuring device that efficiently extracts quantitative thin film thicknesses from a thin film interference image.

It is another object of this invention to provide an interferometric thin film measuring device which extracts quantitative thin film thicknesses based on combined intensity and spectral information from a thin film interference image.

It is another object of this invention to provide a method of measuring thin films using any combination of devices according to the above noted objects.

It is another object of this invention to provide an interferometric method of determining a thin film thickness by generating and accessing a calibrated look-up table that summarizes measured or known properties of a thin film material.

The above and related objects of this invention are realized by providing an interferometric thin film measuring device with an interferometer, a detector, a system calibration unit, a weight vector calculating unit, a look-up table storage unit, a weight vector comparing unit and an output/storage unit. The interferometer has at least a light source which illuminates a thin film with light having substantially preselected spectral and coherence characteristics. More preferably, the interferometer includes optical components to collimate and focus the illumination light, to further select coherence and/or polarization properties, and a beam splitter to redirect the interference pattern to the detector. In the preferred embodiment, the detector digitizes at least a portion of the interference pattern in each of a plurality of image channels. The preferred embodiment uses a filter wheel that has a plurality of color filters arranged therein such that the detector digitizes image data in only one image channel at a given time. However, the broader concept of the invention includes digitizing the interference image either sequentially or simultaneously.

A system calibration unit is in communication with the detector. The system calibration unit calibrates the interferometer and detector system using a thin film with substantially known reflectance properties. In the preferred embodiment, the system calibration unit is implemented on a personal computer or work station. However, the invention includes implementing the system calibration unit as a dedicated hardware component. The system calibration unit is in communication with a weight vector calculating unit. The weight vectors provide approximations to the intensity of the light detected in each of the image channels as a function of thin film thickness. The intensity in each image channel is approximated as a sum over a finite number of orthogonal polynomials in which each orthogonal polynomial is weighted by a coefficient. The coefficients weighting each of the orthogonal polynomials are the components of the weight vector calculated by the weight vector calculating unit. In the preferred embodiment, the orthogonal polynomials are normalized Legendre polynomials. However, the broader concept of the invention includes other conventionally known or specially generated types of orthogonal polynomials and/or functions.

The weight vector calculating unit is similarly implemented on a personal computer, or workstation, and likewise could be implemented as a dedicated hardware component in other embodiments. The weight vector calculating unit is in communication with a weight vector comparing unit and with a lookup table storage unit. The lookup table storage unit stores a plurality of calibration weight vectors as determined from selected calibration thin films. The interferometric thin film measuring device may be used to determine calibration weight vectors based on measurements from selected calibration thin films, or may be based on previously known properties of selected calibration thin films. A plurality of calibration thin film weight vectors are stored in the lookup table storage unit for each of a plurality of calibration thin film thicknesses which are selected to span the thin film thickness range of interest. The lookup table storage unit is implemented in one of the many known mass storage devices conventionally available, such as the hard drive of a personal computer, semiconductor random access memory, or other peripheral mass storage devices such as recordable or rewritable DVD or CD optical discs, magnetic tape storage devices, magneto-optical or phase change optical discs, or floppy disk magnetic drives. However, the lookup table storage unit is not limited to only conventionally known storage units.

The weight vector comparing unit receives a subject weight vector from the weight vector calculating unit and compares it to calibration weight vectors stored in the lookup table storage unit. The weight vector comparing unit is similarly implemented on a personal computer, or workstation, in the preferred embodiment. One skilled in the art would readily recognize that the weight vector comparing unit could also be implemented as a dedicated hardware component. The weight vector comparing unit outputs a thin film thickness corresponding to the calibration weight vector selected from the lookup table storage unit and outputs the determined thin film thickness to an output device and/or a storage unit for later retrieval.

In the interferometric method of determining a thin film thickness according to the invention, calibration data is determined before a thin film thickness is assigned to a subject thin film. In the preferred embodiment, the system is calibrated empirically prior to generating the calibrated lookup table. However, one could also use a system model in order to calibrate the interferometer and detector system based on the system model. After the system is calibrated, a calibration thin film is selected and illuminated by light from the interferometer. Light reflected from the thin film is filtered to produce a plurality of image channels. Light in each of the image channels is detected and a calibration thin film weight vector is determined with each component of the vector associated with one of the image channels for the corresponding selected thin film thickness. In other words, there is a four-dimensional vector associated with the four channels with each component corresponding to one channel in the prefaced embodiment. The calibration thin film weight vectors are used to generate the calibrated lookup table. Another calibration thin film is selected in order to add additional calibration thin film weight vectors to the calibrated lookup table for additional calibration thin film thicknesses. The procedure is repeated until the calibrated lookup table has the desired calibration thin film weight vectors. System calibration data is used in determining each of the calibration thin film weight vectors. The calibrated lookup table can also be generated either from empirical data, as described above, or based on a model.

A subject thin film is illuminated with light from the interferometer. Light reflected from the subject thin film is filtered by a plurality of wavelength filters, such as color filters for visible regions of the spectrum. Light in each of the filter channels is detected and a subject thin film weight vector is determined using both detected light data and data from calibrating the interferometer/detector system. The subject thin film weight vector is compared to calibration thin film weight vectors stored in the calibrated lookup table to select a weight vector from the calibrated lookup table that matches the subject thin film weight vector. The thin film thickness corresponding to the selected calibration weight vector is assigned as the thin film thickness for the subject thin film. The assigned thin film thickness is output to an output device and/or stored for later retrieval.

BRIEF DESCRIPTION OF THE DRAWINGS

These and other objects and advantages of the invention will become more apparent and more readily appreciated by the following detailed description of the presently preferred exemplary embodiment of the invention taken in conjunction with the accompanying drawings, of which.

DETAILED DESCRIPTION OF THE PREFERRED EMBODIMENT

Figure 1:
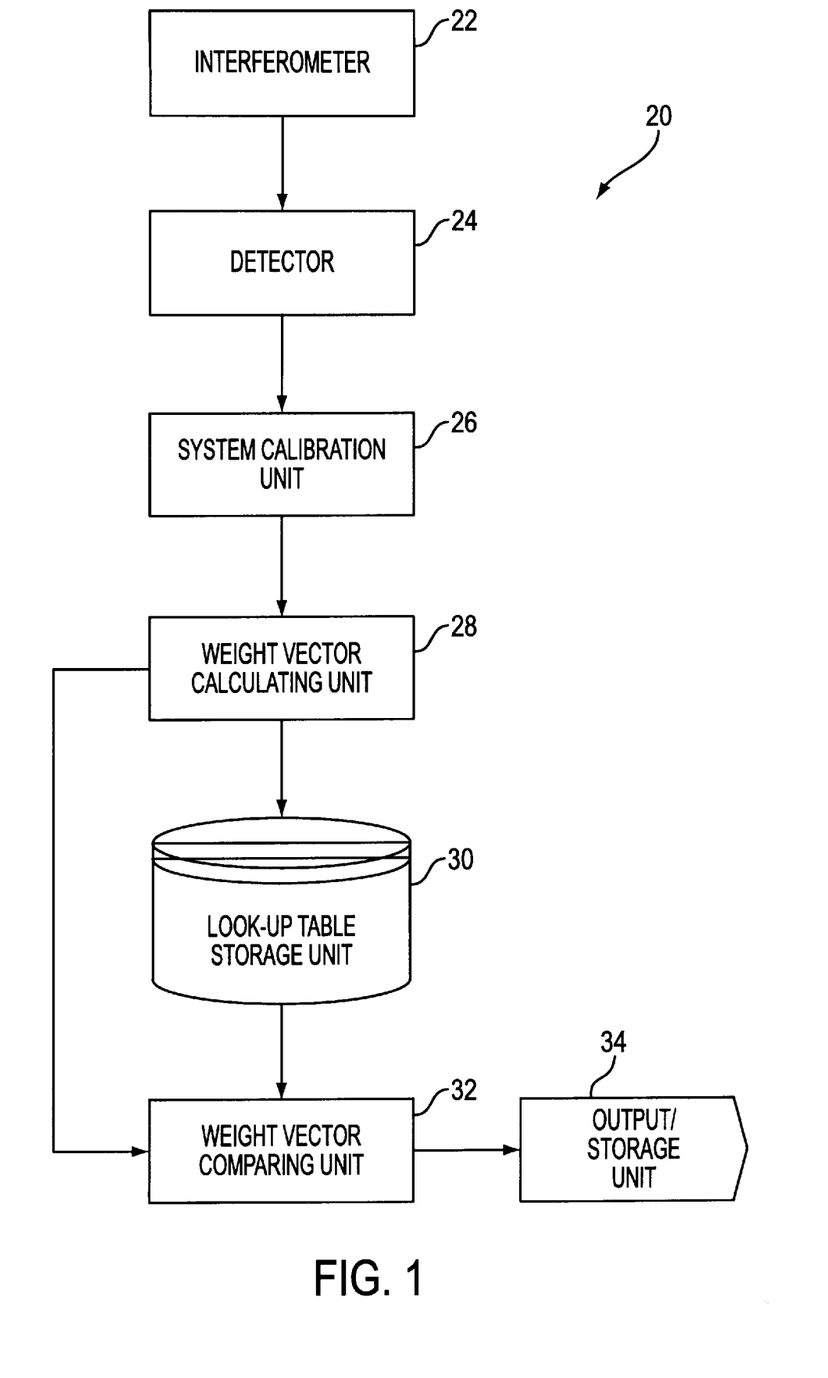
FIG. 1 is a schematic illustration of the interferometric thin film measuring device according to the preferred embodiment of the invention.

The interferometric thin film measuring device according to the present invention is designated generally by reference numeral 20 in FIG. 1. The interferometric thin film measuring device 20 has an interferometer 22, a detector 24, a system calibration unit 26, a weight vector calculating unit 28, a look-up table storage unit 30, a weight vector comparing unit 32, and an output/storage unit 34.

The interferometer 22 may be selected from one of the many known interferometers according to the specific type of thin film measurements desired. In the preferred embodiment, the interferometer 22 is constructed to be suitable for measuring a lipid layer of a tear film of a subject's eye. The preferred embodiment of the interferometric thin film measuring device 20 is shown in more detail in FIG. 2. In the preferred embodiment, the interferometer 22 has a source of illumination light 36, a converging lens 38 to collimate illumination light from the source 36, a converging lens 40 to focus the collimated illumination light onto a thin film, such as the subject's eye 42, and another converging lens 44 disposed in a return path of light reflected from the subject's eye 42 to focus the reflected light onto a detector 24. A beam splitter 46 is disposed between the source of illumination 36 and the subject's eye 42. The beam splitter 46 is partially reflecting, and partially transmitting, and disposed at an angle with respect to light reflected from the observer's eye 42 and collimated by the converging lens 40 such that it reflects a portion of the reflected light by a non-zero angle with respect to the original path of the reflected light to the detector 24.

Figure 2:
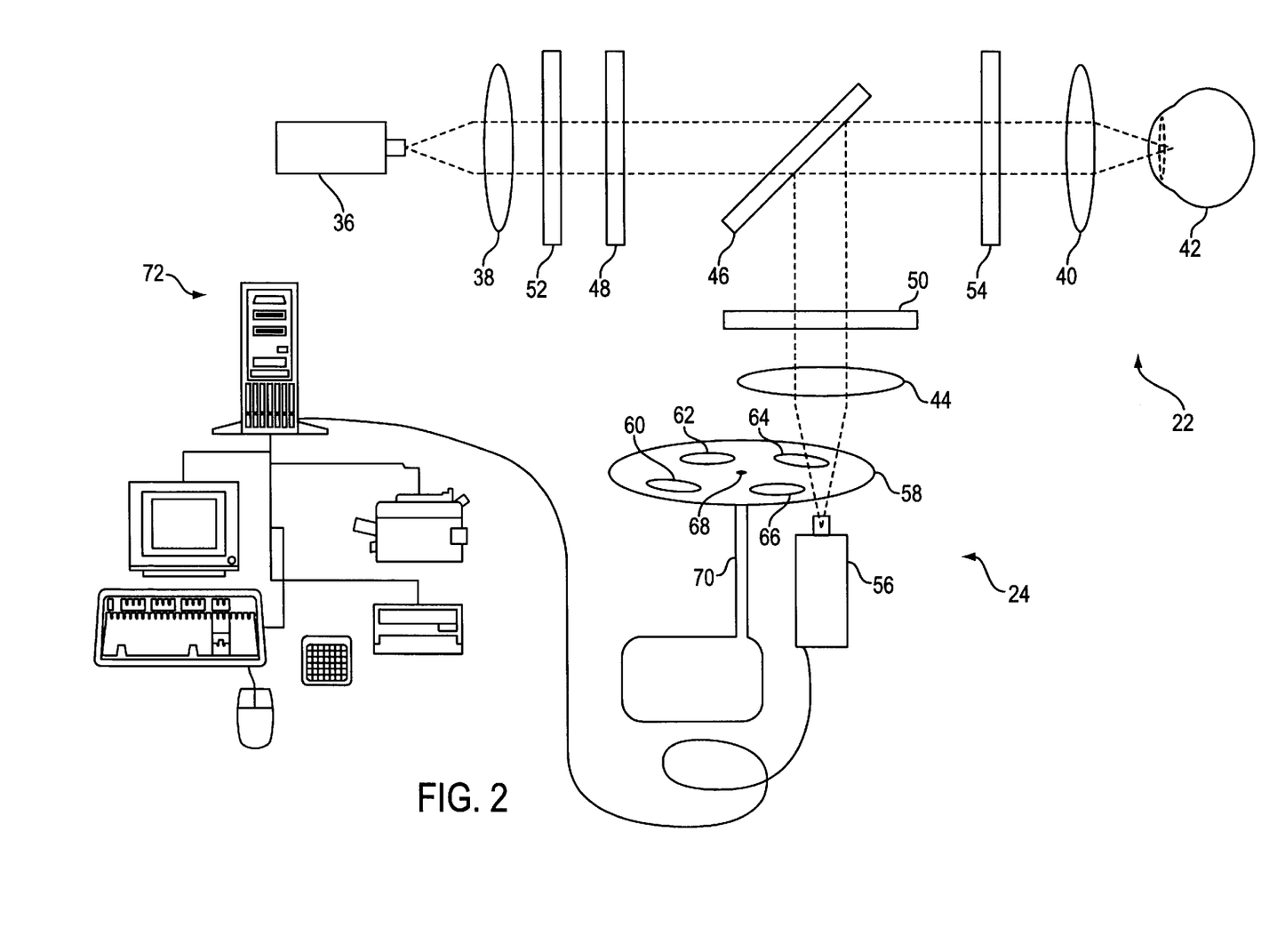
FIG. 2 is a more detailed schematic illustration of the preferred embodiment of the interferometric thin film measuring device according to the preferred embodiment of the invention.

The light source 36 may be selected from a large variety of known light sources which are suitable for use with interferometers. In the preferred embodiment, the light source is selected to have illumination light in at least a plurality of frequency bands in the visible region of the electromagnetic spectrum. However, one may select sources of illumination radiation in other regions of the electromagnetic spectrum for other specific applications of this invention, e.g., infrared or ultraviolet sources of illumination. A tungsten-halogen light source is a suitable light source in the preferred embodiment since it has a relatively flat spectrum across the visible region. However, the invention is not limited to only tungsten-halogen light sources. One may select various other light sources such as other gas emission sources, or coherent sources such as laser light sources. For example, one may select a tunable laser, such as a tunable dye laser which can be selectively tuned to a plurality of frequencies within the visible region of the spectrum. One may also select a plurality of lasers which emit light in different regions of the spectrum.

The converging lenses 38, 40 and 44 may be simply single lenses, or compound lenses, depending on the optical performance required for the particular application.

In the preferred embodiment, the interferometer 22 includes a polarizer 48 disposed in the optical path between the source of illumination light 36 and the beam splitter 46. Another polarizer 50 is disposed in the return path between the beam splitter 46 and the detector 24. A diffuser 52 is disposed between the converging lens 38 and the polarizer 48. The preferred embodiment of the interferometer 22 also includes a quarter wave plate or retarder 54 disposed between the beam splitter 46 and the converging lens 40.

The detector 24 includes a video camera 56 and optical filters 58 in the preferred embodiment. Preferably, the video camera 56 is a camera, either a digital camera which has CCD sensors, or an analog camera with a digitizing device that provide a digital output signal. A suitable filter 58 is a filter wheel which has four color filters 60, 62, 64, and 66. The filter wheel 58 is rotatable about its center 68 on an axle 70 such that each filter 60, 62, 64, and 66 may be rotated to intercept light reflected from the subject's eye 42 and focused on the camera 56. With this arrangement, light is detected in each of four image channels after being filtered, sequentially, by each of the four filters 60, 62, 64 and 66. However, the invention is not limited to only detecting light sequentially in different image channels. The general concept of the invention anticipates other mechanisms for defining both sequential image channels, and for measuring reflected light simultaneously in separate image channels.

The filter unit 58 is not limited to having four color filters. However, four color filters are currently preferred since this permits one to select color filters from currently available filters in such a way as to span the whole visible spectrum, yet minimize the overlap between any two of the filters. Suitable filters include, but are not limited to Wratten 25, 47A, 57A and 96 filters.

In the preferred embodiment, the video camera 56 is in communication with a personal computer 72. The system calibration unit 26, weight vector calculating unit 28 and weight vector comparing unit 32 (illustrated in FIG. 1) are all implemented by programming the personal computer 72, or alternatively a work station, in the preferred embodiment. However, the invention is not limited to implementing the system calibration unit 26, weight vector calculating unit 28, and weight vector comparing unit 32 by programming a personal computer 72. In other embodiments, one could provide dedicated hardware components in order to optimize the performance of the interferometric thin film measuring device, but likely at a higher cost. The look-up table storage unit 30 is similarly implemented on a personal computer 72 in the preferred embodiment of the invention. The look-up table storage unit 30 is preferably stored in the computer memory, such as RAM, and/or on the computer's hard drive. However, the broader concepts of the invention anticipate the use of other storage devices such as recordable or rewritable CD drives, DVD units, or tape drives. Furthermore, one could provide a dedicated storage unit for the look-up table storage unit 30 in order to optimize performance and/or storage capacity.

The following physical model of the interferometer 22 and detection system 24 facilitates the detailed description of the system calibrating unit 26, weight vector calculating unit 28, look-up table storage unit 30 and weight vector comparing unit 32. The output of the interferometer 22 and detector 24 can be represented as $$t_i(d) = \int_{\lambda_1}^{\lambda_2} f_i(\lambda) c(\lambda) o(\lambda) l(\lambda) r(\lambda, d) d\lambda + \varepsilon_i \quad (i = 1, 2, \ldots, m) \tag{1}$$

where $f_i$ is the transmittance of filter i, $c(\lambda)$ is the sensitivity of the CCD array, $O(\lambda)$ is the transmittance of the optical path, $l(\lambda)$ is the spectrum of the illumination light, $r(\lambda,d)$ is the reflectance of the thin film and $\varepsilon_i$ is the measurement noise. This equation is written generally for any number of filters m. In the specific example illustrated in FIG. 2, there are four filters, thus corresponding to the case with m=4. The integration from $\lambda_1$ to $\lambda_2$ in Equation (1) is taken over the region of the electromagnetic spectrum applicable to the detector 24. Since the camera 56 and filters 60, 62, 64 and 66 were selected to span the visible region of the spectrum, the integration in Equation (1) can be taken over the visible region of the spectrum. The reflectance $r(\lambda,d)$ is a function of both the wavelength $\lambda$ and the thickness d of the thin film. Since the integration is over wavelength, the output of the interferometer 22 and detector 24 remains a function of the thickness d of the thin film.

The system model represented by Equation (1) can be written in terms of a matrix equation by approximating the continuous wavelength parameter $\lambda$ as N equally spaced wavelength values. This leads to the matrix equation $$t = (FCOL)r + e \tag{2}$$

where t is a column matrix that has m components, each being for one of the image channels. F is an m×N matrix in which each element of the matrix corresponds to the transmittance of a corresponding filter at a discrete wavelength value, with the transmittance of a specific color filter extending across a given row of the matrix F. The reflectance array r is a column vector with N components corresponding to the N discrete wavelengths. In Equation (2), C, O, and L are diagonal N×N matrices with the discrete samples of $c(\lambda)$, $O(\lambda)$ and $l(\lambda)$ extending along the respective diagonals, and e is a column vector of the additive measurement noise in which each element of the column vector e is for a respective one of the m image channels.

We can rewrite Equation (2) in a simpler form as $$t = Sw + e \tag{3}$$

where w=Lr and S=FCO. The matrix w lumps together the illuminance of the illumination light and the reflectance from the thin film. The system matrix S describes the spectral characteristics for each channel of the optical system, comprising a color filter, optical path and the camera. In particular, each row of system matrix S is the product of the transmittances of one color filter, optical path and the camera, referred to as the sensitivity vector of the channel.

The system calibration unit 26 determines a sensitivity vector for each image channel of the system. In the preferred embodiment, a tungsten-halogen light source is used for the source of illumination light since it has a relatively flat spectrum. A conventional, standard calibration reflectance map is used as the test object for calibration. Preferably, several measurements at each thickness are used such that the system calibration unit can take advantage of a least-squares formulation for reducing sensitivity to various sources of noise, including quantization error. In the preferred embodiment, the system calibration unit 26 performs a least squares minimization to determine a suitable system matrix $S_{opt}$, $$S_{opt} = \arg\min_S \left( \sum_{q=1}^{Q} \| t_q - S w_q \|^2 \right) \tag{4}$$

where Q≧N is the number of measurements. Other norms based on Equation (3) may be minimized to arrive at a suitable solution in other embodiments of the invention. The solution to Equation (4) is obtained by the principal eigenvector method, known in the art, in the preferred embodiment. To derive the solution, we define $W = [w_1, W_2, \ldots W_Q]$ as the N×Q matrix of source and target reflection data. We define $W = U\Sigma V^T$ as the singular value decomposition of W, where U and V are the matrices of left and right singular vectors and $\Sigma$ is the matrix of singular values $$\Sigma = [\text{diag}(\sigma_1, \sigma_2, \ldots, \sigma_N), O_{N \times (K-N)}]. \tag{5}$$

We can estimate the sensitivity vector from $$\hat{s}_j = \sum_{i=1}^{P} \frac{v_i^T \tau_j}{\sigma_i} u_i \quad (j = 1, 2, 3 \ldots, m) \tag{6}$$

where $u_i$ and $v_i$ are columns of U and V, respectively, $\{\hat{s}_j\}_{1 \leq j \leq m}$ are the estimated rows of the matrix S, and $\{\tau_j\}_{1 \leq j \leq m}$ are rows of the m×Q measurement matrix $T = [t_1, t_2, \ldots t_Q]$. The summation is performed using P≦ (rank of W) singular values and vectors. The system calibration unit 26 thus provides the estimated sensitivity vector of each of the m image channels for the interferometer 22 and detector 24 with a light source having known spectral characteristics, for example a tungsten-halogen light source, and a test object with substantially known reflectance characteristics, such as a standard calibration reflectance map.

The weight vector calculating device 28 provides weight vectors which are coefficients to a finite set of orthogonal polynomials which together provide an approximation to the intensity of the light reflected from the thin film. The intensity of the reflected light is related to the system model of Equation (1) according to $$I(\lambda,d) = l(\lambda) r(\lambda,d). \tag{7}$$

In the preferred embodiment, the orthogonal functions are normalized Legendre polynomials, however, the scope and spirit of the invention is not limited to only the use of Legendre polynomials as the orthogonal basis functions. The intensity of the reflected light represented by Equation (7) is approximated as $$\tilde{I}(\lambda, d) = \sum_{i=1}^{n} a_i(d) p_i(\lambda), \tag{8}$$

where $p_i(\lambda)$ are the n Legendre polynomials, and $a_i(d)$ are the n weight vectors corresponding to the set of n Legendre polynomials. By representing the reflected intensity as a sum over n orthogonal polynomials, such as Legendre polynomials, weighted by components of the weight vector, the system model represented by Equation (1) can then be represented as $$t(d) = Ka(d), \quad (9)$$

where the matrix K has m×n matrix elements $$k_{ij} = \int_{\lambda_1}^{\lambda_2} s_i(\lambda) p_j(\lambda) d(\lambda) \quad (10)$$

and $t(d)=[t_1(d), t_2(d), \ldots, t_m(d)]^T$. The superscript "T" stands for the operation of transposing the matrix, thus t(d) is a column vector of m filter outputs. For n discrete wavelengths, we can write K as K=SP, where the columns of the N×m matrix P are evaluated from the Legendre polynomials. The left hand side of Equation (9) represents the output from the interferometer 22 and detector 24 in the m image channels.

The weight vector calculating unit 28 determines weight vectors represented as a(d) in Equation (9). In the case where the number of image channels m is equal to the number of basis functions n, the weight vector calculating unit 28 determines the weight vectors as can be represented by the equation $$a = K^{-1} t. \quad (11)$$

If the number of image channels m exceeds the number of basis functions n, the weight vector calculating unit 28 calculates the weight vectors by evaluating the matrix equation $$a = (K^T K)^{-1} (K^T t). \quad (12)$$

In other words, the weight vector calculating unit 28 determines weight vectors in the preferred embodiment by calculating the product of the matrices in the right hand side of Equation (11) or Equation (12), depending on whether m=n or whether m>n. The matrix K, and its associated transpose and inverse matrices, are known from the output from the system calibration unit 26 and from the specific set of basis functions selected. The matrix t represents output data from the detector 24.

The look-up table storage unit 30 stores a plurality of weight vectors output from the weight vector calculating unit 28. In the preferred embodiment, weight vectors are stored for a plurality of discrete thin film thicknesses. The weight vector comparing unit 32 compares an output weight vector from the weight vector calculating unit 28 with the plurality of stored weight vectors in the look-up table storage unit 30 in order to find the closest stored weight vector in the look-up table storage unit 30. Once a weight vector from the look-up table storage unit is selected as being closest to the weight vector output from the weight vector calculating unit 28, the weight vector comparing unit outputs a thin film thickness corresponding to the selected weight vector from the look-up table storage unit 30.

The vector comparing unit 32 selects the weight vector from the look-up table storage unit 30 that is closest to the output weight vector from the weight vector calculating unit 28 as represented by a modified homogenous distance formula. The modified homogeneous distance formula can be expressed as $$dist(a_1, a_2) = \sqrt{(a_1 - a_2)^T \Lambda^{-1} (a_1 - a_2)} \quad (13)$$

where $\Lambda = \sigma^2 (K^T K)^{-1}$ is the covariance matrix of the Legendre polynomial coefficients. The distance is minimized by the vector comparing unit 32 in the preferred embodiment in order to select the weight vector in the look-up table storage unit 30 that is closest to the output weight vector from the weight vector calculating unit 28. One skilled in the art will recognize that criteria other than that of the preferred embodiment may be used in order to select a matching weight vector from the look-up table storage unit 30 without departing from the broader concepts of the invention. The thin film thickness determined by the weight vector comparing unit is sent to the output/storage unit 34. The output/storage unit 34 may be a video monitor or may be a storage unit such as a hard drive, tape or a form of optical drive or other data storage medium.

The details of the system calibration unit 26, weight vector calculating unit 28, look-up table storage unit 30 and vector comparing unit 32 were described above with regard to one point on the image sensor of the video camera 56. In the preferred embodiment, the video camera 56, which is preferably a digital camera with a CCD array, or an analog camera with a digitizing device that provides digital output signals, outputs data for a plurality of regions across the CCD array. The above procedures are repeated for a plurality of regions across the CCD array to produce a thin film thickness contour and/or surface map.

In operation, the source of illumination light 36 provides light which is collimated by the converging lens 38, diffused by diffuser 52 and polarized by polarizer 48. A portion of the diffused and polarized light passes through the beam splitter 46, through the retarder 54, and is focused by the converging lens 40 onto a thin film 42. Some light incident on the thin film 42 reflects from the top surface of the film, while some light travels through the thin film and reflects from the interface of the thin film and an underlying material to return back through the thin film. Light reflected from both the top surface and the back surface of the thin film add coherently if the coherence length of the light is equal to or greater than the two way path traveled through the thin film. Light reflected from the thin film 42 returns through and is collimated by the condenser lens 40. The reflected light passes through the retarder 54 and a portion is reflected by the beam splitter 46 such that the light reflected from the thin film 42 and beam splitter 46 travels along a path directed away from the illumination path. The light reflected from the thin film 42 and beam splitter 46 then passes through polarizer 50 and is focused by condenser lens 44 to pass through one of the color filters 60, 62, 64, or 66 to be detected by the video camera 56.

The video camera 56 preferably outputs a signal for a plurality of regions of the incident image. In the preferred embodiment, the filter wheel 58 is rotated to align one of the color filters 60, 62, 64, 66 to filter the light directed onto the video camera 56. This procedure is repeated until data is collected in each of the four color channels, in the preferred embodiment. The system calibration unit 26 determines the sensitivity vectors for the interferometer 22 and detector 24 in each of the image channels. The weight vector calculating unit 28 calculates weight vectors, using calibration vectors from the system calibration unit for a preselected set of orthogonal basis functions, according to Equations (11) or (12) for each region of the image detected by the video camera 56. The look-up table storage unit 30 stores weight vectors for a plurality of calibration thin film thicknesses for each of the plurality of regions detected by the video camera 56. The weight vector comparing unit obtains a weight vector from a weight vector calculating unit 28 and compares it to the weight vectors in the look-up table storage unit 30 based on minimizing the distance in the measurement space represented by Equation (13) in the preferred embodiment. The weight vector comparing unit 32 then outputs a thin film thickness corresponding to the weight vector from the weight vector calculating unit 28 and directs it to the output/storage unit 34.

Figure 3:
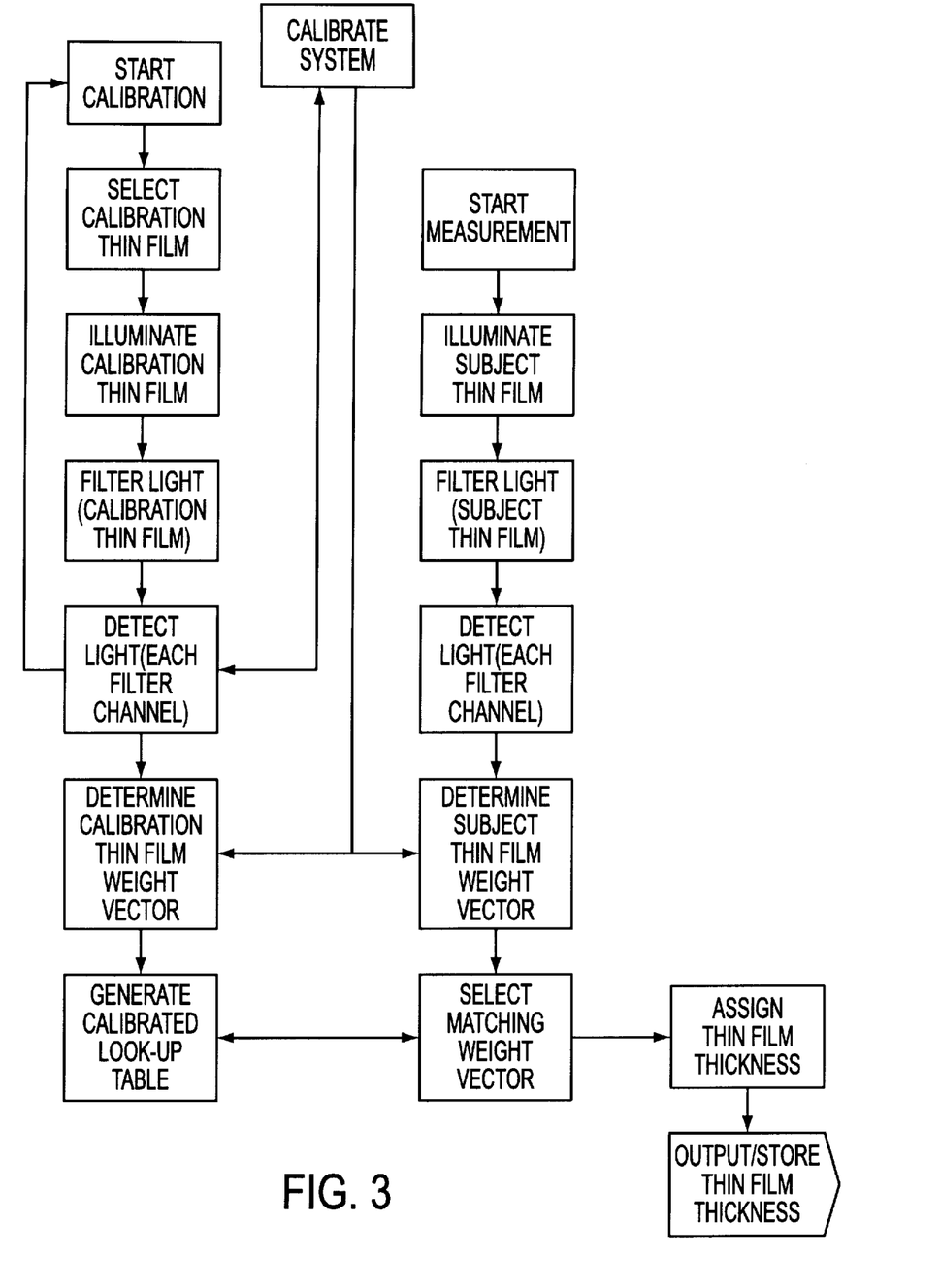
FIG. 3 is a flow chart illustrating the interferometric method of determining a thin film thickness according to the preferred embodiment of the invention.

In the method according to the preferred embodiment of the invention, the system that includes the interferometer 22 and detector 24 is calibrated with a source of illumination light that has substantially known intensity and spectral characteristics and a test object that has a substantially known reflectance. FIG. 3 is a flow chart that helps to illustrate the method according to the preferred embodiment of the invention.

After calibrating the interferometer 22 and detector 24 system, one selects a calibration thin film which has a substantially known thin film thickness. Preferably, the calibration thin film is a material which has substantially the same, similar, or a substantially known relationship to an anticipated subject thin film. The calibration thin film is illuminated with light having substantially predetermined intensity and spectral characteristics and a coherence length that is approximately equal to, or longer than, the thickness of the calibration thin film. Light reflected from the calibration thin film is filtered with a plurality of wavelength filters, such as color filters. Light from each filter channel is detected. A calibration weight vector is then determined for the selected calibration thin film using sensitivity vectors determined in the system calibration along with a preselected set of orthogonal polynomials and the output from detected light in each filter channel.

The calibration vector for the calibration thin film is used to generate a calibrated look-up table. If the calibrated look-up table does not sufficiently cover the desired range of calibration weight vectors, another calibration thin film is selected, illuminated, filtered, detected and another weight vector is determined to generate a calibrated look-up table that includes a weight vector for the newly selected calibration thin film. This process is repeated to produce calibration weight vectors to span the thin film thickness range of interest. In addition, the difference in thicknesses of the calibration thin films may be selected to be small or large depending on the desired measurement precision. The calibration thin films may be selected to span a desired range of thin film thickness at a substantially constant thickness interval, or at varying thickness intervals, in other embodiments.

For performing real-time measurements, at least a portion of the calibrated look-up table has to be generated prior to taking measurements of a subject thin film. Alternatively, post-processing may be performed by recording the thin film images as conventional digital images. The subject thin film is illuminated with light having substantially the same predetermined intensity and spectral characteristics as was used to illuminate the calibration thin films. Light reflected from the subject thin film is filtered preferably with the same plurality of wavelength filters used to generate the calibrated look-up table. Light from each of the plurality of image channels is detected and a weight vector of the subject thin film is determined for the preselected plurality of orthogonal polynomials and with the sensitivity vectors output from the calibration of the interferometer 22 and detector 24. A calibration weight vector from the calibrated look-up table is selected to be substantially the most equivalent calibration weight vector to the subject weight vector. In the preferred embodiment, the metric represented by Equation (13) is minimized in order to select the calibration weight vector.

In some applications one may construct and store a plurality of calibration tables with each calibration table corresponding to a different optical setup. For example, one may construct systems with different light sources and/or filter combinations such that each is tuned to have a better sensitivity in a particular thin film thickness range. The filters, detectors and light sources may be used to extend across a broader portion of the electromagnetic spectrum than just the visible portion. Other CCD cameras are suitable for use with this invention, such as the TEKTRONIX 200K which covers a range of 300–1100 nm. Furthermore, Edmund's Scientific wavelength filters that are currently available in the range of 334–1064 nm may also be used in specific applications of this invention. However, the invention is not limited to only those components which are currently available.

In other embodiments, one may use a filter wheel with a larger number of filters than four, for example, to permit the user to select various combinations of filters, which are preferably taken four at a time. Each selection is made in a way to optimize system sensitivity and thin film thickness accuracy with respect to a specific thickness range (e.g., one for 0–50 nm, another for 50–100 nm, and yet another for 100–150 nm instead of just one configuration for the whole thickness range of 0–150 nm). Each configuration is calibrated separately in this embodiment to determine its weight vectors and the lookup table.

Figure 4:
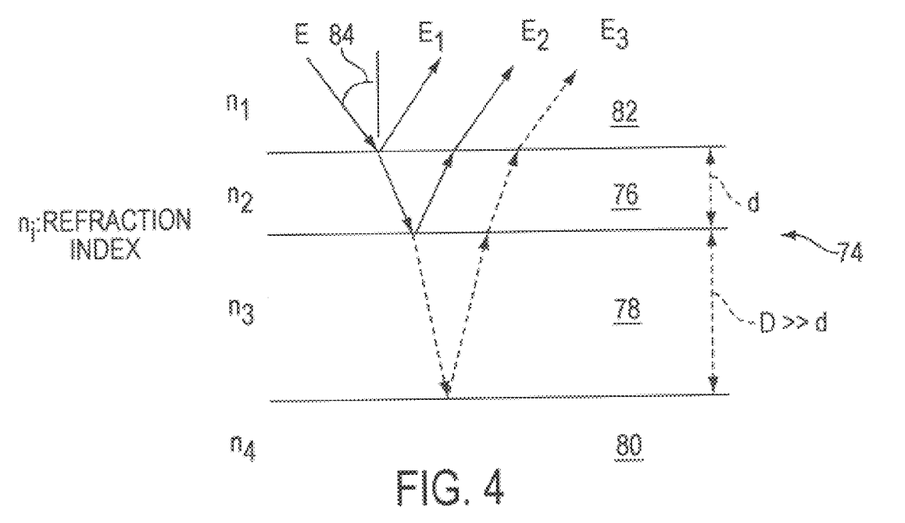
FIG. 4 is a schematic illustration of a cross-sectional view of a small region of the tear film of a subject's eye.

A description of a computer simulation of the performance of the preferred embodiment of the invention as applied to a specific example of determining the thickness of the lipid layer of a tear film follows. FIG. 4 shows a schematic illustration of a greatly enlarged portion of a subject's eye. The tear film 74 has a sub-structure of a thin lipid layer 76 and a tear fluid layer 78. Typically, the tear fluid layer 78 is much thicker than the lipid layer 76. The tear film 74 covers a region of the cornea 80 of the subject's eye. The outer surface of the lipid layer 76 is exposed to air 82. The refractive index of air 82 is represented by $n_1$, the index of refraction of the lipid layer 76 is represented by $n_2$, the index of refraction of the tear fluid is represented by $n_3$ and the index of refraction of the cornea 80 is represented by $n_4$.

The ray diagram in FIG. 4 helps to explain the interference effect. In a small local region of the subject's eye, the incident light at a particular wavelength $\lambda$ may be represented as a plane wave $$E(\lambda) = A(\lambda)e^{j\left[\frac{2\pi c}{\lambda}t - \frac{2\pi z}{\lambda} + \phi(\lambda)\right]} \tag{14}$$

where $A(\lambda)$ is the component of incident light at $\lambda$, $\phi(\lambda)$ is the phase, c is the speed of light, z is the direction of propagation and t is time. The reflected light from the surface of the lipid layer is $$E_1(\lambda) = A(\lambda)f_1 e^{j\left[\frac{2\pi c}{\lambda}t - \frac{2\pi z}{\lambda} + \phi(\lambda)\right]}, \tag{15}$$

where $$f_1 = \frac{n_2 - n_1}{n_2 + n_1}$$

depends on the refractive indices $n_1$ and $n_2$ of air and the lipid layer, respectively. The ray depicted as $E_2$ in FIG. 4 is the portion of the incident light E that traverses the lipid layer 76, reflects from the boundary between the lipid layer 76 and the tear fluid 78, and travels back through the lipid layer 76 to emerge into the air 82. The light $E_2$ reflected from the boundary between the lipid layer 76 and the tear fluid 78 can be represented as $$E_2(\lambda) = A(\lambda) f_2 f_3 f_4 e^{j\left[\frac{2\pi c}{\lambda}t - \frac{2\pi z}{x} + \phi(\lambda)\right]} e^{-j\delta}, \quad (16)$$

$$f_2 = \frac{2n_1}{n_2 + n_1}, \quad f_3 = \frac{n_3 - n_2}{n_3 + n_2}, \quad f_4 = \frac{2n_2}{n_1 + n_2}. \quad (17)$$

If the incident light E is substantially normal to the surface between the lipid layer 76 and air 82, the phase lag is approximately $$\delta = \frac{4\pi d n_2}{\lambda}. \quad (18)$$

In other words, if the angle 84 is substantially zero, then the phase lag is given by Equation (18). The cornea 80 produces less specular reflection than the lipid layer 76 and the tear fluid layer 78. Consequently, the ray $E_3$ will generally be much weaker than the rays $E_1$ and $E_2$. This is represented schematically in FIG. 4 by using a dotted line for the ray $E_3$. Furthermore, since the thickness D of the tear fluid 78 is much greater than the thickness d of the lipid layer 76, one may select a light source and/or otherwise arrange optical components such that the coherence length of the incident light E is less than the two-way path through the tear film 74. However, the light source and/or optical components are selected such that the coherence length of the light E is approximately equal to or greater than the two-way travel distance of light through the lipid layer 76. The rays $E_1$ and $E_2$ thus add coherently while the weak ray $E_3$ would have a random phase relation with respect to rays $E_1$ and $E_2$ at any given time. Thus ignoring the ray $E_3$, the intensity of the interference pattern becomes $$I(\lambda,d) = |E|^2 = |E_1|^2 + |E_2|^2 + E^*_1 E_2 + E_1 E^*_2 = A^2(\lambda)[f_1^2 + f_2^2 f_3^2 f_4^2 + 2 f_1 f_2 f_3 f_4 \cos \delta(\lambda,d)], \quad (19)$$

where the asterisk denotes complex conjugation. One can see from Equation (19) that a transmittance of the thin film varies according to the thickness of the thin film and the refractive indices of the thin film and surrounding media.

Figure 5:
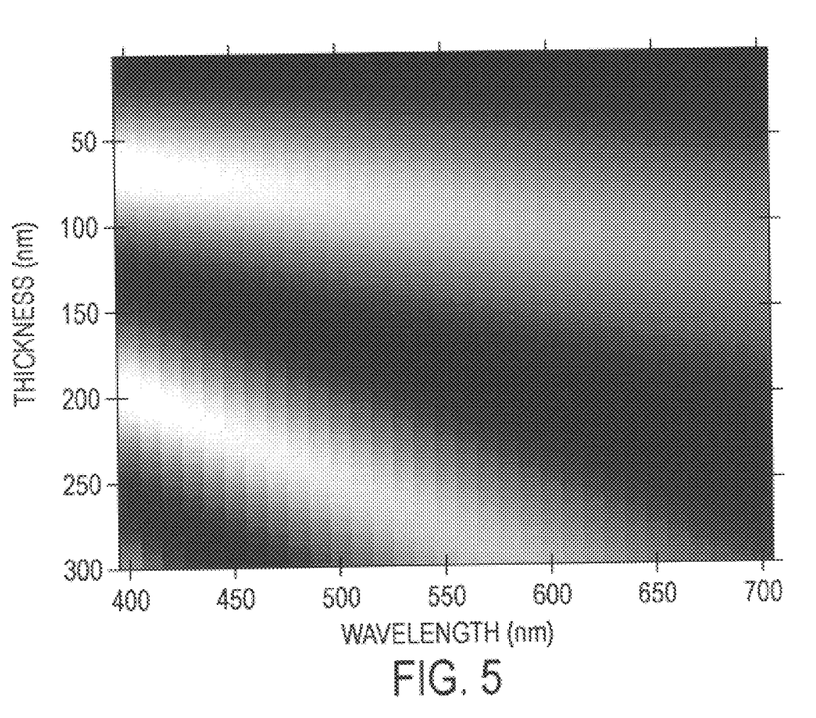
FIG. 5 illustrates the spectrum of the fringe patterns for a thin lipid layer illuminated by tungsten-halogen light.
Figure 6A:
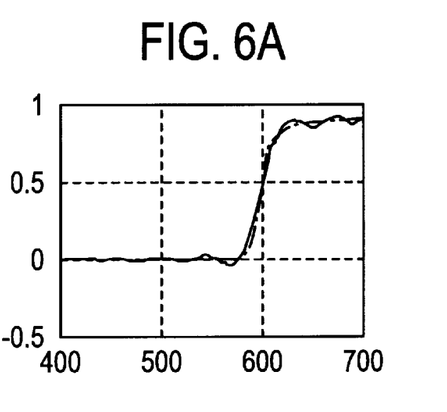
FIGS. 6A, 6B, 6C and 6D compare the actual transmittance to the estimated transmittance for each of four image channels for a particular example of the preferred embodiment of the invention.
Figure 6B:
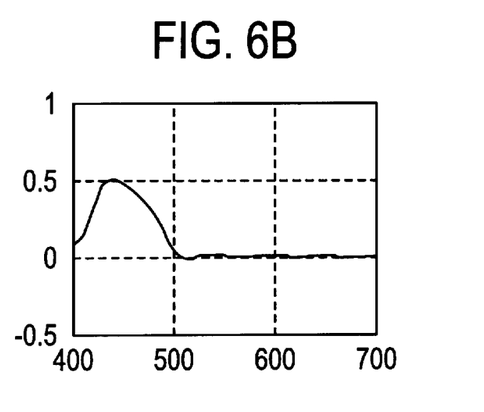
Figure 6C:
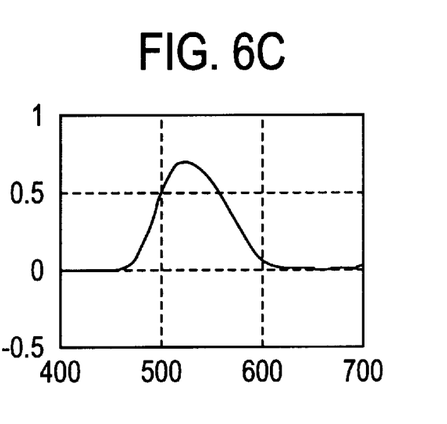
Figure 6D:
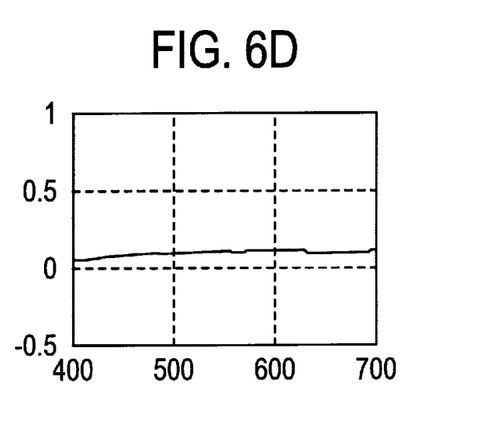

The lipid layer for a normal eye has an average thickness less than 100 nm and a index of refraction of 1.4766. The average thickness of the tear fluid for a normal eye is believed to be less than 10 $\mu$m (about 1–10 $\mu$m) and an index of refraction of 1.334. FIG. 5 illustrates an interference spectrum for the thin film lipid layer illuminated by a tungsten-halogen light source. Thicknesses are shown in the range from 0 to 300 nm. Each horizontal line in the FIGURE corresponds to a particular thickness of the lipid layer. If one selects a horizontal line in FIG. 5 somewhere in the range between 50 and 100 nm one will see that as it extends across the range of wavelengths, the magnitude of the associated component varies slowly. This is in contrast to a horizontal line at 250 nm, for example, in which it varies rapidly from the dark region to bright regions back to dark regions as one follows the horizontal line across the FIGURE. This indicates that such thin films with a thickness of 250 nm produce well defined color fringe patterns. On the other hand, lipid layers with thicknesses between 100 nm and 50 nm do not produce well defined color fringes. Rather, they produce intensity variations that one may describe as shades of gray. This illustrates that both intensity and color provide useful information in determining thin film thicknesses. The device and methods according to this invention permit one to use intensity and color information simultaneously in determining thin film thicknesses. It is not essential to the device and methods of this invention to have completely constructive and/or completely destructive interference to be able to determine thin film thicknesses.

The following example simulates the performance of the interferometric thin film measuring device and method according to the preferred embodiment of the invention. The light source is assumed to be a tungsten-halogen lamp and four Wratten filters (25, 47, 57A, and 96) are used in the example. In addition, the spectral sensitivity of the video camera 56 is taken to be that of a SONY XC-77 video camera. FIGS. 6A–6D show the estimated sensitivities for the four image channels as the dashed line compared to the respective actual transmittance indicated as a solid line.

Figure 7:
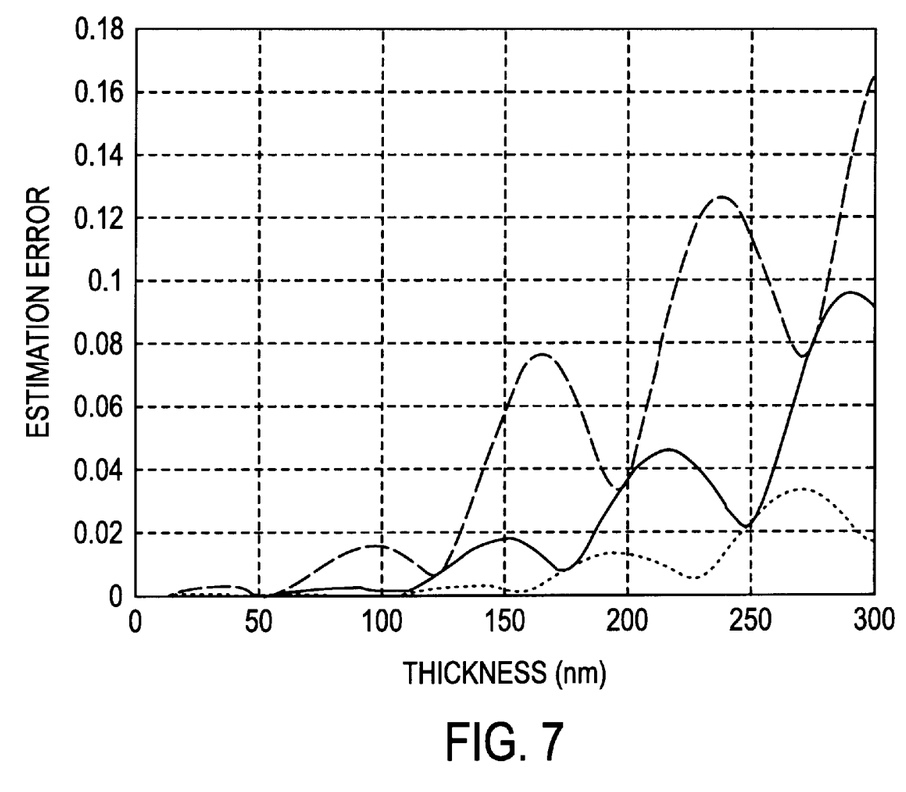
FIG. 7 shows normalized estimation errors for the case of n equal to 3, 4, and 5 Legendre polynomials.

FIG. 7 shows the normalized error, defined as $$dist(I(\lambda, d), \tilde{I}(\lambda, d)) = \sqrt{\int_{\lambda_1}^{\lambda_2} [I(\lambda, d) - \tilde{I}(\lambda, d)]^2 d\lambda}, \quad (20)$$

where $I(\lambda,d)$ is the ideal spectrum given by Equation (19), and $\tilde{I}(\lambda,d)$ is the estimated spectrum as represented by Equation (8). The dashed line in FIG. 7 is for the case in which there are n=3 Legendre polynomials in the summation represented by Equation (8), the solid line is the case for n=4 Legendre polynomials, and the dotted line is the case for n=5 Legendre polynomials. The estimated errors in FIG. 7 are normalized by the norm of the ideal spectrum. The peak error regions are directly related to regions where the spectrum varies rapidly (see, FIG. 5). In the preferred embodiment, the number of image channels, defined by the number of filters, has to be equal to or exceed the number of Legendre polynomials (i.e., m≧n). Since four Wratten filters are used in this example of the preferred embodiment, this requires that there be n≦4 Legendre polynomials. As one may readily see from FIG. 7, selecting n=4 Legendre polynomials will minimize the estimation error for the case of 4 image channels.

Figure 8A:
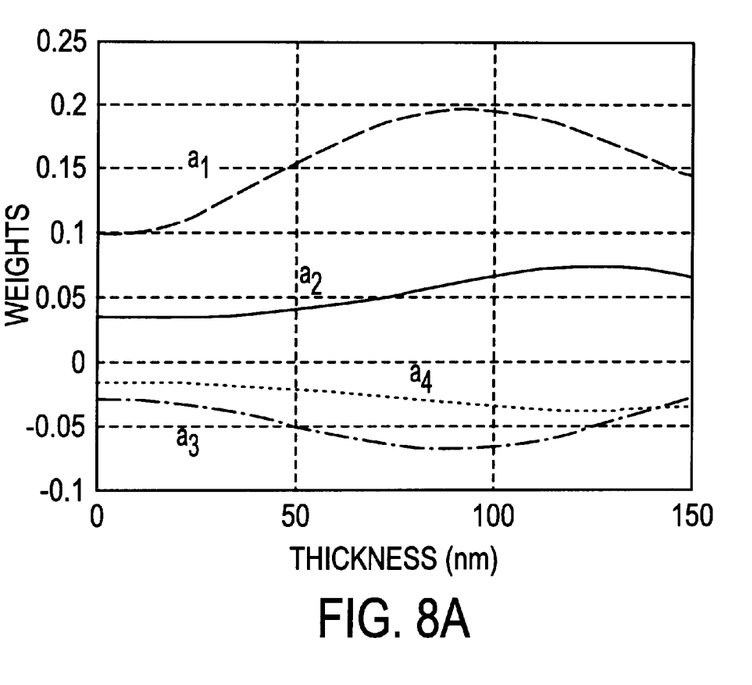
FIG. 8A illustrates calibration table lookup data for an example according to the preferred embodiment of the invention.

A calibrated lookup table is generated in this example by taking the index of refraction for the thin film to be that of the average lipid material and selecting calibration thin films in the range of 0 to 150 nm. The calibration thin film weight vectors for the corresponding thicknesses are determined in accordance to Equation (11) since n=m in this example. FIG. 8A is a graphical representation of the calibrated lookup table for this example of the preferred embodiment. Each of the four components of the calibration thin film weight vector is shown in FIG. 8A for the range of thin film thickness between 0 and 150 nm. The components of the calibrated thin film weight vector $a_1$, $a_2$, $a_3$, and $a_4$, in this example, are the coefficients of the Legendre polynomials in the estimation represented by Equation (8). According to the preferred embodiment of the invention, by selecting a weight vector at a corresponding thin film thickness d, one only has to match a small number of components (four in this example). This can be done without establishing a selection criterion based only on intensity or only on wavelength. Selecting a weight vector from the calibrated look-up table simultaneously utilizes both intensity and wavelength information. In the regions below 100 nm, in this example, intensity information will be the dominant factor in the calibration thin film weight vectors. Color information will become more important along with the intensity information at a thin film thickness of around 100 nm, in this example, and will become even more important for greater thicknesses where distinct color fringe patterns are generated.

Figure 8B:
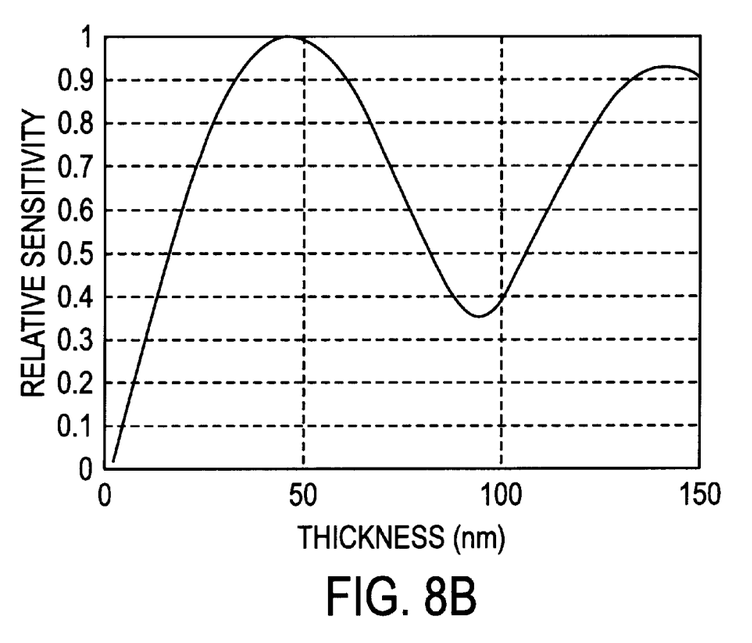
FIG. 8B illustrates the relative sensitivity in an example according to the preferred embodiment of the invention.

FIG. 8B illustrates the relative sensitivity of the norm of the calibration thin film weight vectors. A higher sensitivity means more attenuation of the unorganized noise effects. FIG. 8B thus shows good sensitivity over the thickness range of interest in this example.

Figure 9A:
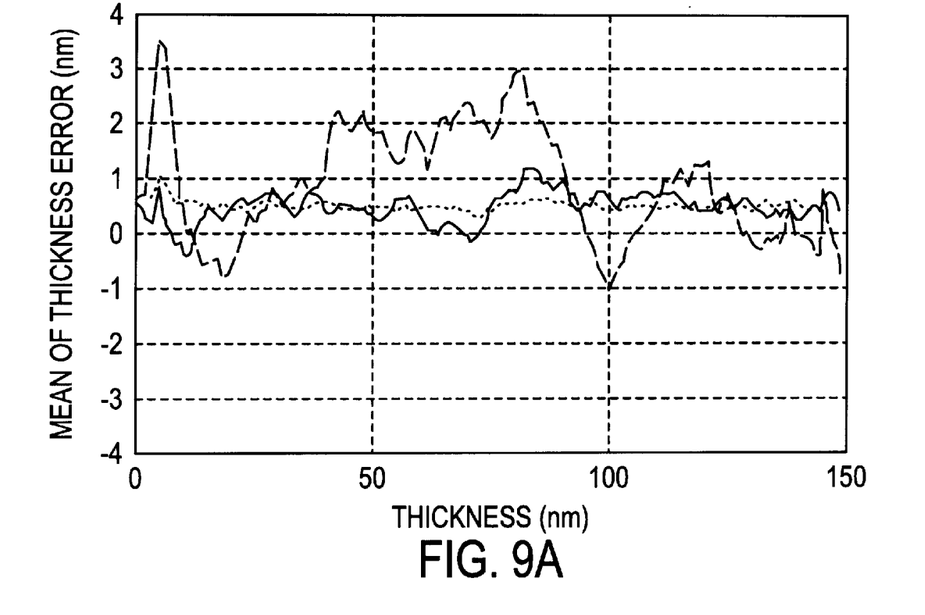
FIG. 9A illustrates simulated mean thickness errors according to an example of the preferred embodiment of the invention for three different signal-to-noise ratios.
Figure 9B:
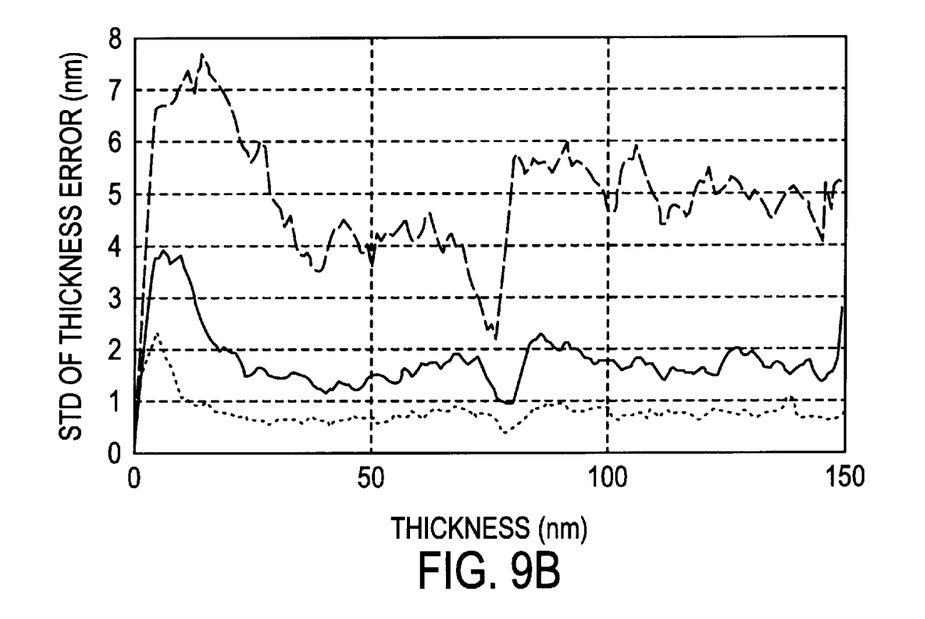
FIG. 9B illustrates the standard deviation thickness errors corresponding to the simulations of FIG. 9A.
Figure 10A:
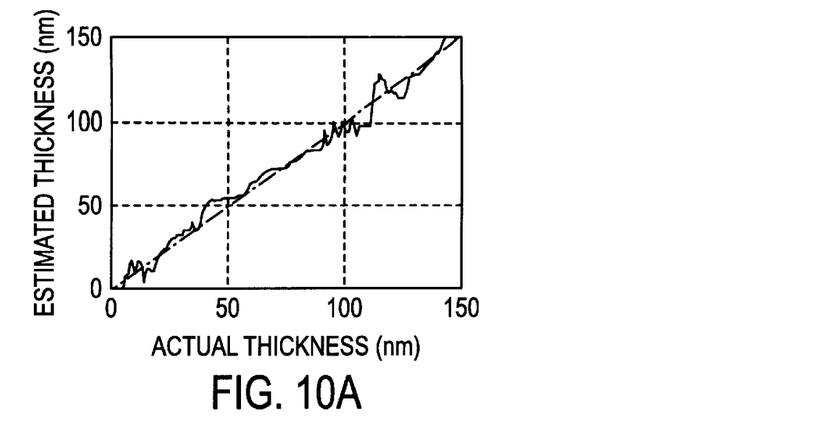
FIGS. 10A, 10B and 10C show one example of the estimated thickness versus actual thin film thicknesses for signal-to-noise ratios of 30 dB, 40 dB, and 50 dB, respectively.
Figure 10B:
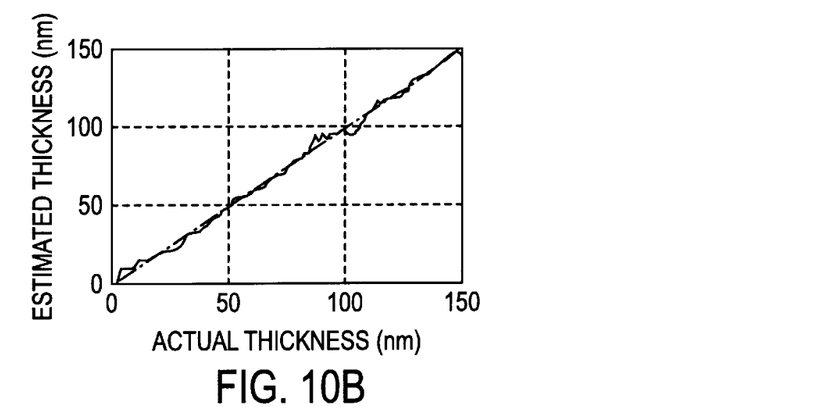
Figure 10C:
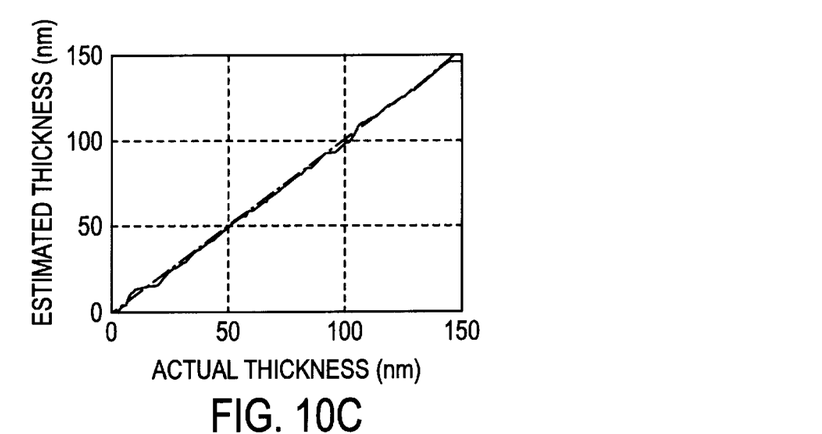

FIG. 9A shows the mean of the thickness error as a function of the thin film thickness. The dashed, solid, and dotted lines correspond to signal-to-noise ratios of 30 dB, 40 dB and 50 dB, respectively. FIG. 9B illustrates the standard deviation of the extracted thickness error for the thin film thickness range of 0 to 150 nm. The dashed line, solid line and dotted line correspond to signal-to-noise ratios of 30 dB, 40 dB and 50 dB, respectively. The mean and standard deviations illustrated in FIGS. 9A and 9B were determined by evaluating 100 simulations of thickness extraction with various levels of camera noise for each thin film thickness. The signal-to-noise ratio (SNR) was determined according to $$SNR = 10 \log\left[\frac{\text{trace}(Sww^T S^T)}{m\sigma^2}\right] \qquad (21)$$

where $\sigma^2$ is the variance of the noise. FIGS. 10A, 10B and 10C compare the actual thin film thickness to the thin film thicknesses determined according to the preferred embodiment of this invention, again for various levels of measurement noise, for a selected example taken from the 100 simulations performed by the inventors to obtain the statistical error characteristics of the method. FIG. 10A corresponds to a SNR=30 dB, FIG. 10B corresponds to SNR=40 dB, and FIG. 10C corresponds to SNR=50 dB.

This example is an application of the preferred embodiment of the invention to the case in which the thin film is the lipid layer of a subject's eye. In this example, the calibration look-up table was generated based on a physical model of the optical properties of lipid thin films. However, the invention is not limited to generating the calibrated look-up table based on only physical models. Alternatively, one can generate a calibrated look-up table empirically for cases in which the thin film material is not well understood, or if it has complex properties.

Once a calibrated look-up table has been generated, one may determine the thin film thickness even in cases where there aren't well defined interference fringes. This is particularly useful in the example of applying the preferred embodiment to the measurement of lipid layers of a subject's eye, since the lipid layer changes its thickness over time and is often so thin that it does not produce well defined fringes. Since there are only four components for each calibrated weight vector, and correspondingly the subject's thin film weight vector, the thickness extraction can be performed quickly in real time as the lipid layer of the subject's eye changes. Furthermore, since the video camera 56 measures the interference pattern over an extended area, a thickness map over the lipid layer can be generated, also in real time if desired.

Although the above example applies the preferred embodiment to the case of measuring a lipid layer thickness of a subject's eye, the preferred embodiment is generally applicable to other cases where it is desirable to measure thin film thicknesses in real time and/or map the thin film thicknesses over spatial regions. For example, one skilled in the art would recognize that the device and method according to this invention has many other applications such as measuring thin films on optical components or semiconductors.

Although only a single embodiment has been described in detail above, along with a specific example of applying the preferred embodiment, one skilled in the art will readily appreciate that many modifications are possible in this exemplary embodiment without materially departing from the novel teachings and advantages of this invention. All such modifications are intended to be included within the scope of this invention, as defined in the following claims.

What is claimed is:

1. An interferometric method of determining a thin-film thickness, comprising:

selecting a plurality of calibration thin films, each having a predetermined film thickness;

illuminating each of said plurality of calibration thin films with light having substantially predetermined intensity and spectral characteristics and a coherence length approximately equal to or longer than each corresponding predetermined film thickness;

filtering light reflected from each of said plurality of calibration thin films with a plurality of wavelength filters;

detecting light in a plurality of image channels, wherein each image channel of said plurality of image channels contains light output from a respective one of said wavelength filters;

determining a plurality of calibration weight vectors for each of a plurality of look-up thicknesses within a range of look-up thicknesses that includes at least some of said predetermined film thicknesses of said plurality of calibration thin films, said calibration weight vectors collectively containing both frequency and intensity information of said light reflected from said plurality of calibration thin films;

generating a calibrated look-up table comprising said calibration weight vectors;

illuminating a subject thin film with light having said substantially predetermined intensity and spectral characteristics and said coherence length;

filtering light reflected from said subject thin film with each of said plurality of wavelength filters;

detecting light in a plurality of image channels, wherein each image channel of said plurality of image channels contains light output from a respective one of said wavelength filters after said filtering light reflected from said subject thin film;

determining a subject weight vector from light detected from said plurality of image channels of said subject thin film;

selecting a calibration weight vector from said look-up table that is substantially the most equivalent calibration weight vector to said subject weight vector; and determining said subject thin-film thickness from said selected calibration weight vector.

2. An interferometric method of determining a thin-film thickness according to claim 1, wherein said calibration weight vectors of said look-up table and said subject weight vector determined from said subject thin film are weight functions of a plurality of orthogonal polynomials, and an inner product of each of said calibration weight vectors and said plurality of orthogonal polynomials provides an approximation of a corresponding thin-film interference pattern intensity.

3. An interferometric method of determining a thin-film thickness according to claim 2, wherein said orthogonal polynomials are Legendre polynomials.

4. An interferometric method of determining a thin-film thickness according to claim 2, wherein the number of said plurality of orthogonal polynomials is equal to the number of said plurality of image channels.

5. An interferometric method of determining a thin-film thickness according to claim 2, wherein the number of said plurality of orthogonal polynomials is less than the number of said plurality of image channels.

6. An interferometric method of determining a thin-film thickness according to claim 4, wherein the number of said plurality of orthogonal polynomials and the number of said plurality of image channels is less than five.

7. An interferometric method of determining a thin-film thickness according to claim 5, wherein the number of said plurality of orthogonal polynomials is less than five.

8. An interferometric method of determining a thin-film thickness according to claim 4, wherein the number of said plurality of orthogonal polynomials and the number of said plurality of image channels is equal to four.

9. An interferometric method of determining a thin-film thickness according to claim 1, wherein said selecting a calibration weight vector from said look-up table includes finding a magnitude for a difference vector between said calibration weight vector and said subject weight vector for each of a plurality of said look-up thicknesses, and said determining said measurement thin-film thickness assigns a thickness based on a minimization of said difference vector magnitudes.

10. An interferometric method of determining a thin-film thickness according to claim 9, wherein said finding a magnitude for a difference vector includes weighting components of said difference vector to account for different signal-to-noise ratios in different ones of said plurality of image channels.

11. An interferometric method of determining a thin-film thickness according to claim 9, wherein said minimization of said difference vector magnitudes assigns a look-up thickness corresponding to the smallest one of said difference vector magnitudes.

12. An interferometric method of determining a thin-film thickness according to claim 1, wherein said detecting light in a plurality of image channels detects light with a digital camera which outputs a digital signal.

13. An interferometric method of determining a thin-film thickness according to claim 12, wherein said determining a plurality of calibration weight vectors and said determining a subject weight vector comprises processing said digital signal with a weight vector calculating device.

14. An interferometric method of determining a thin-film thickness according to claim 1, further comprising repeating said illuminating a measurement thin film, filtering light reflected from said measurement thin film, detecting light in a plurality of image channels, determining said weight vector, selecting a calibration weight vector from said look-up table, and determining said measurement thin film a plurality of times to measure a thin film-thickness over a time interval in real time.

15. An interferometric method of determining a thin-film thickness according to claim 1, wherein said predetermined intensity and spectral characteristics of said light includes spectral components in a plurality of regions of the visible spectrum.

16. An interferometric method of determining a thin-film thickness according to claim 1, wherein said thin film is a lipid layer of an eye, and said coherence length of said light is preselected to be less than a two-way optical path length between a top and a bottom surface of a tear film below said lipid layer.

17. An interferometric thin film measuring device, comprising:
  a source of illumination light;
  a detector disposed in a return path of light reflected from a specimen disposed in a path of said illumination light;
  a plurality of wavelength filters disposed in said return path of light reflected from said specimen between said specimen and said detector;
  a weight vector calculating device in communication with said detector;
  a look-up table storage unit in communication with said weight vector calculating device;
  a weight vector comparing unit in communication with said look-up table storage unit and said weight vector calculating device; and
  a data output unit in communication with said weight vector comparing unit.

18. An interferometric thin film measuring device according to claim 17, further comprising:
  a beam splitter disposed in said path of said illumination light;
  a first polarizer disposed in said path of said illumination light between said source of illumination light and said beam splitter; and
  a second polarizer disposed in said return path of light between said beam splitter and said detector.

19. An interferometric thin film measuring device according to claim 18, further comprising:
  a first converging lens unit disposed in said path of said illumination light between said source of illumination light and said beam splitter;
  a second converging lens unit disposed in said path of illumination light and said return path between said specimen and said beam splitter; and
  a third converging lens unit disposed between said beam splitter and said detector in said return path.

20. An interferometric thin film measuring device according to claim 17, wherein said source of illumination light has spectral components in a plurality of regions of the visible spectrum.

21. An interferometric thin film measuring device according to claim 20, wherein said plurality of wavelength filters are four color filters, each transmitting light predominantly in a different region of the visible spectrum such that they substantially span the visible spectrum.

22. An interferometric thin film measuring device according to claim 17, further comprising a diffuser disposed in said path of said illumination light between said source of illumination light and said beam splitter.

23. An interferometric thin film measuring device according to claim 21, further comprising a diffuser disposed in said path of said illumination light between said source of illumination light and said beam splitter.

24. An interferometric thin film measuring device according to claim 21, wherein said four color filters are fixed in a filter wheel disposed proximate to said return path of light, said four color filters thereby being selectably rotatable into and out of said return path.

25. An interferometric method of determining a thin-film thickness, comprising:

illuminating a subject thin film with light having substantially predetermined intensity and spectral characteristics and coherence length;

filtering light reflected from said subject thin film with each of a plurality of wavelength filters;

detecting light in a plurality of image channels, wherein each image channel of said plurality of image channels contains light output from a respective one of said wavelength filters after said filtering light reflected from said subject thin film;

determining a subject weight vector from light detected from said plurality of image channels of said subject thin film;

selecting a calibration weight vector from a look-up table comprising a plurality of calibration weight vectors, said calibration weight vector being substantially the most equivalent calibration weight vector to said subject weight vector; and determining said subject thin-film thickness from said selected calibration weight vector.

26. An interferometric method of determining a thin-film thickness according to claim 25, wherein said calibration weight vectors are determined empirically from calibration thin films.

27. An interferometric method of determining a thin-film thickness according to claim 25, wherein said calibration weight vectors are determined theoretically based on a physical model of calibration thin films.

28. An interferometric method of determining a thin-film thickness according to claim 1, wherein said detecting light in a plurality of image channels detects light with an analog camera and digitizer providing a digital output signal.

29. An interferometric thin film measuring device according to claim 18, further comprising a quarter-wave plate or retarder disposed in said path of said illumination light between said beam splitter and said specimen.

30. An interferometric thin film measuring device according to claim 18, wherein said source of illumination light provides illumination light in a visible region of the electromagnetic spectrum.

31. An interferometric thin film measuring device according to claim 18, wherein said source of illumination light provides illumination light in an infrared region of the electromagnetic spectrum.

32. An interferometric thin film measuring device according to claim 17, wherein said source of illumination light has spectral components in a plurality of infrared regions of the electromagnetic spectrum.

33. An interferometric thin film measuring device according to claim 32, wherein said plurality of wavelength filters each transmit light predominantly in a different infrared region of the electromagnetic spectrum.

34. An interferometric method of determining a thin-film thickness according to claim 1, wherein said predetermined intensity and spectral characteristics of said light includes spectral components in a plurality of infrared regions of the electromagnetic spectrum.

* * * * *